(12) United States Patent
Bi

(10) Patent No.: US 8,334,099 B2
(45) Date of Patent: Dec. 18, 2012

(54) NUCLEIC ACID AMPLIFICATION USING A REVERSIBLY MODIFIED OLIGONUCLEOTIDE

(76) Inventor: Wanli Bi, San Ramon, CA (US)

(*) Notice: Subject to any disclaimer, the term of this patent is extended or adjusted under 35 U.S.C. 154(b) by 0 days.

(21) Appl. No.: 12/375,100

(22) PCT Filed: Jul. 30, 2007

(86) PCT No.: PCT/US2007/017015
§ 371 (c)(1),
(2), (4) Date: May 6, 2009

(87) PCT Pub. No.: WO2008/016562
PCT Pub. Date: Feb. 7, 2008

(65) Prior Publication Data
US 2010/0021970 A1   Jan. 28, 2010

Related U.S. Application Data

(60) Provisional application No. 60/834,410, filed on Jul. 31, 2006.

(51) Int. Cl.
*C12Q 1/68* (2006.01)
*C07H 21/04* (2006.01)

(52) U.S. Cl. .................... 435/6.12; 536/24.33
(58) Field of Classification Search ............. 435/6, 91.2; 536/24.31, 24.32, 24.33
See application file for complete search history.

(56) References Cited

U.S. PATENT DOCUMENTS

| | | | |
|---|---|---|---|
| 5,270,184 A | 12/1993 | Walker | 435/91 |
| 5,338,671 A | 8/1994 | Scalice | 435/91.2 |
| 5,411,876 A | 5/1995 | Bloch | 435/91.2 |
| 5,413,924 A | 5/1995 | Kosak | 435/177 |
| 5,427,930 A | 6/1995 | Birkenmeyer | 435/91.52 |
| 5,565,339 A | 10/1996 | Bloch | 435/91.2 |
| 5,643,764 A | 7/1997 | Kosak | 435/91.1 |
| 5,677,152 A | 10/1997 | Birch | 435/91.2 |
| 5,693,502 A | 12/1997 | Gold | 435/91.2 |
| 5,700,642 A * | 12/1997 | Monforte et al. | 435/6 |
| 5,763,173 A | 6/1998 | Gold | 435/6 |
| 5,773,258 A | 6/1998 | Birch | 435/6 |
| 5,837,450 A | 11/1998 | Dahlberg | 435/6 |
| 5,846,717 A | 12/1998 | Brow | 435/6 |
| 5,854,033 A | 12/1998 | Lizard | 435/91.2 |
| 5,874,557 A | 2/1999 | Gold | 536/23.1 |
| 5,916,779 A | 6/1999 | Pearson | 435/91.2 |
| 5,952,180 A | 9/1999 | Ju | 435/6 |
| 5,985,557 A | 11/1999 | Prudent et al. | 435/6 |
| 6,001,567 A | 12/1999 | Brow | 435/6 |
| 6,001,611 A | 12/1999 | Will | 435/91.2 |
| 6,020,130 A | 2/2000 | Gold | 435/6 |
| 6,037,130 A | 3/2000 | Tyagi | 435/6 |
| 6,090,543 A | 7/2000 | Prudent | 435/6 |
| 6,183,960 B1 | 2/2001 | Lizardi | 435/6 |
| 6,183,967 B1 | 2/2001 | Jayasena | 435/6 |
| 6,183,998 B1 | 2/2001 | Ivanov | 435/91.2 |
| 6,210,884 B1 | 4/2001 | Lizardi | 435/6 |
| 6,251,639 B1 | 6/2001 | Kurn | 435/6 |
| 6,344,329 B1 | 2/2002 | Lizardi | 435/6 |
| 6,348,314 B1 | 2/2002 | Prudent | 435/6 |
| 6,355,432 B1 | 3/2002 | Fodor | 435/6 |
| 6,403,341 B1 | 6/2002 | Barnes | 435/91.2 |
| 6,410,278 B1 | 6/2002 | Notomi | 435/91.1 |
| 6,432,642 B1 | 8/2002 | Livak | 435/6 |
| 6,509,157 B1 * | 1/2003 | Martinez | 435/6 |
| 6,511,810 B2 | 1/2003 | Bi | 435/6 |
| 6,794,142 B2 | 9/2004 | Laird | 435/6 |
| 2003/0162199 A1 * | 8/2003 | Bonner | 435/6 |

FOREIGN PATENT DOCUMENTS

| | | |
|---|---|---|
| WO | WO 94/04548 | 3/1994 |
| WO | WO 96/07669 | 3/1996 |
| WO | WO 96/39414 | 12/1996 |
| WO | WO 02/100873 | 12/2002 |

OTHER PUBLICATIONS

Boute N, Jockers R, Issad T. (2002) The use of resonance energy transfer in high-throughput screening: BRET versus FRET. Trends Pharmacol Sci. 23(8): 351-354.
Chan TW, Fung YM, Li YC. (2002) A study of fast and metastable dissociations of adenine-thymine binary-base oligonucleotides by using positive-ion MALDI-TOF mass spectrometry. Am Soc Mass Spectrom. 13(9): 1052-1064.
Kaiser MW, Lyamicheva N, Ma W, Miller C, Neri B, Fors L, Lyamichev VI. (1999) A comparison of eubacterial and archaeal structure-specific 5'-exonucleases. J Biol Chem. 274(30): 21387-21394.
Lawyer FC, Stoffel S, Saiki RK, Chang SY, Landre PA, Abramson RD, Gelfand DH. (2003) High-level expression, purification, and enzymatic characterization of full-length *Thermus aquaticus* DNA polymerase and a truncated form deficient in 5' to 3' exonuclease activity. PCR Methods Appl. 2(4): 275-287.
Lawyer FC, Stoffel S, Saiki RK, Myambo K, Drummond R, Gelfand DH. (1989) Isolation, characterization, and expression in *Escherichia coli* of the DNA polymerase gene from *Thermus aquaticus*. J Biol Chem. 264(11): 6427-6437.
Leone G, van Schijndel H, van Gemen B, Kramer FR, Schoen CD. (1998) Molecular beacon probes combined with amplification by NASBA enable homogeneous, real-time detection of RNA. Nucleic Acids Res. 26(9): 2150-2155.
Nadeau JG, Pitner JB, Linn CP, Schram JL, Dean CH, Nycz CM. (1999) Real-time, sequence-specific detection of nucleic acids during strand displacement amplification. Anal Biochem. 276(2): 177-187.

(Continued)

*Primary Examiner* — Prabha Chunduru
(74) *Attorney, Agent, or Firm* — Ballard Spahr LLP

(57) ABSTRACT

The present invention provides a method for amplification of a target nucleic acid sequence or signal, wherein an amplification reaction mixture is used which contains at least one reversibly modified oligonucleotide having a non-hydroxyl group 3' end which can be converted into a hydroxyl 3' end upon exposure to a chemical and/or irradiation and/or a range of temperature. The present invention also provides a reversibly modified oligonucleotide as described above, and a nucleic acid amplification reaction mixture and kit comprising such an oligonucleotide.

25 Claims, 6 Drawing Sheets

OTHER PUBLICATIONS

Nilsson M, Gullberg M, Dahl F, Szuhai K, Raap AK. (2002) Real-time monitoring of rolling-circle amplification using a modified molecular beacon design. Nucleic Acids Res. 30(14): e66.

Nurmi J, Ylikoski A, Soukka T, Karp M, Lövgren T. (2000) A new label technology for the detection of specific polymerase chain reaction products in a closed tube. Nucleic Acids Res. 28(8): E28.

Nutiu R, Li Y. (2002) Tripartite molecular beacons. Nucleic Acids Res. 30(18): e94.

Spears PA, Linn CP, Woodard DL, Walker GT. (1997) Simultaneous strand displacement amplification and fluorescence polarization detection of *Chlamydia trachomatis* DNA. Anal Biochem. 247(1): 130-137.

Walker GT, Linn CP, Nadeau JG. (1996) DNA detection by strand displacement amplification and fluorescence polarization with signal enhancement using a DNA binding protein. Nucleic Acids Res. 24(2): 348-353.

International Search Report for PCT/US2007/017015 dated May 30, 2008.

International Preliminary Report on Patentability (including Written Opinion) for PCT/US2007/017015 dated Feb. 3, 2009.

Communication pursuant to Article 94(3) EPC for EP Application No. 07836334.8 dated Jun. 2, 2009.

Response to Examination Report for EP Application No. 07836334.8 dated Oct. 1, 2009.

First Examination Report for IN Application No. 177/MUMNP/2009 dated May 6, 2010.

\* cited by examiner

| Multiplex | # Primers | #Amplicons | #PDs |
|---|---|---|---|
| 1 | 2 | 1 | 1 |
| 2 | 4 | 2 | 6 |
| 3 | 6 | 3 | 15 |
| 4 | 8 | 4 | 28 |
| 5 | 10 | 5 | 45 |
| 6 | 12 | 6 | 66 |
| 7 | 14 | 7 | 91 |
| 8 | 16 | 8 | 120 |
| 9 | 18 | 9 | 153 |
| 10 | 20 | 10 | 190 |

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence = Synthetic
      Construct

<400> SEQUENCE: 1
ccgtctgtgc cttctcatct g                                              21

<210> SEQ ID NO 2
<211> LENGTH: 20
<212> TYPE: DNA
```

```
<213> ORGANISM: Artificial Sequence
<220> FEATURE:
<223> OTHER INFORMATION: Description of Artificial Sequence = Synthetic
      Construct

<400> SEQUENCE: 2
ggtttccatg taacgtgcag                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence = Synthetic
      Construct

<400> SEQUENCE: 3
ggtctccatg cgacgtgcag                                                    20
```

NUCLEIC ACID AMPLIFICATION USING A REVERSIBLY MODIFIED OLIGONUCLEOTIDE

CROSS-REFERENCE TO RELATED APPLICATIONS

The present application is a National Phase Application of International Application No. PCT/US2007/017015, filed Jul. 30, 2007, which claims priority to U.S. Patent Application No. 60/834,410 filed Jul. 31, 2006, which applications are incorporated herein fully by this reference.

FIELD OF THE INVENTION

The present invention is generally related to the field of nucleic acid chemistry. More specifically, it relates to methods of amplifying nucleic acid sequences or signals and to methods of reducing non-specific amplification.

BACKGROUND

Nucleic acid amplification technologies are widely used in clinical microbiology, blood screening, food safety, genetic disease diagnosis and prognosis, environmental microbiology, drug target discovery and validation, forensics, and other biomedical research. Robustness of nucleic acid amplification, specificity, sensitivity, reliability in terms of accuracy and precision, and affordability are of particular importance.

Nucleic acid sequence specific amplification allows sensitive detection of the presence of a specific sequence. Polymerase chain reaction (PCR) and ligase chain reaction (LCR) are two thermocycling amplification technologies.

In contrast PCR and LCR, isothermal amplification refers to a category of amplification in which amplification is carried out at a substantially constant temperature. Transcription-mediated amplification (TMA), nucleic acid sequence based amplification (NASBA), strand-displacement amplification (SDA), rolling circle amplification (RCA), single primer isothermal amplification (SPIA™), and exponential single primer isothermal amplification (X-SPIA™), self-sustained sequence replication (3SR) and loop mediated isothermal amplification (LAMP) are examples of isothermal amplification. Nucleic acid sequence can also be detected through signal amplification process, such as cycling probe and invader assay. Detectable signal is generated by nuclease cleavage of hybridized probe.

Because all enzymes, regardless its thermostability, are active in a range of temperature, such property could adversely affect nucleic acid amplification in terms of specificity, sensitivity and signal/noise ratio etc. This has been clearly demonstrated in PCR process. A thermostable DNA polymerase is essential for a PCR. Although optimal temperature of catalytic activity of a thermostable DNA polymerase is around 60~75° C., it is also active at low temperature. It retains significant activity even at room temperature. Its activity at low temperature is a cause of primer dimer formation, non-specific amplification and reduced detection sensitivity.

Performance of DNA PCR is improved by employing hot-start technologies. "Hot start" refers to any method for assembling PCR reactions that keeps one or more of the reaction components physically or functionally separate from the rest of the components at low temperature and that allows the onset of the reactions at an elevated temperature. Hot-start PCR technologies are categorized into the following groups:

1. Physical barrier to divide all essential components into at least two compartments as disclosed in U.S. Pat. Nos. 5,411,876, 5,565,339; 5,413,924 and 5,643,764, all of which are incorporated herein by reference. The barrier is removed by heating at elevated temperature.
2. Reversible enzyme inhibitors to suppress enzyme activity at low temperature as disclosed in U.S. Pat. Nos. 5,338,671; 5,677,152; 5,773,258; 6,183,998; 5,693,502, 5,874,557, 5,763,173, 6,020,130, and 6,183,967, all of which are incorporated herein by reference. Binding of the inhibitor is either non-covalent or covalent. Hot-start by these methods is homogeneous and is the most widely used.
3. Phase separation of cofactor as disclosed in U.S. Pat. No. 6,403,341, incorporated herein by reference. $Mg^{2+}$ is precipitated at low temperature and becomes soluble as temperature rises.

One-step RT PCR is a process of amplifying RNA target by combining reverse transcribing RNA molecule and amplifying complementary DNA molecule in one vial. Target RNA molecules include HIV, HCV, West Nile Virus (WNV), human influenza virus, avian flu virus, Dengue virus, Ebola virus etc. In the United States, it is mandatory to test presence of HIV, HBV, HCV and WNV in donor blood. Performance of one-step RT PCR is critical to these clinical tests and blood screening. Unfortunately none of the existing hot-start technologies can be well applied to this process because:

1. Most reverse transcriptase, the key enzyme for reverse transcription, can't be a target for hot-start process because they are not thermostable and will lose activity after incubation at high temperature.
2. RNA molecule, the subject of the testing, is not stable and undergoes significant degradation at high temperature. Presence of divalent metal ion, such as $Mg^{2+}$ makes the degradation much severer. None of the existing technologies could be applied without damaging target RNA molecules.
3. Long time incubation of reverse transcription process, usually 30 minutes or longer, tremendously increases chance of having side reactions that could reduce detection sensitivity dramatically. This shows that enzyme inhibitor based hot-start technology would not improve performance of one-step RT PCR.

Because of practical importance of nucleic acid amplification, there is strong demand for a novel technology which can improve performance of the nucleic acid amplification reaction, especially one-step RT PCR In this application a novel controlled start of nucleic acid amplification reaction is described. All patents, patent applications, and publications mentioned herein, both supra and infra, are incorporated herein by reference.

SUMMARY OF THE INVENTION

The inventors find that there has not been a hot-start technology involving oligonucleotides, and that as an essential component for nucleic acid amplification, oligonucleotide is an ideal target for hot-start or controlled start technologies.

The present invention provides a method for amplification of a target nucleic acid sequence or signal, wherein an amplification reaction mixture is used which contains at least one reversibly modified oligonucleotide having a non-hydroxyl group 3' end which can be converted into a hydroxyl 3' end upon exposure to a chemical and/or irradiation and/or a range of temperature.

The present invention also provides a method for amplification of a target nucleic acid sequence or signal, comprising the steps of:

(a) contacting a sample suspected of containing the target nucleic acid with an amplification reaction mixture containing at least one reversibly modified oligonucleotide, wherein said reversibly modified oligonucleotide has a non-hydroxyl group 3' end which can be converted into a hydroxyl 3' end upon exposure to a chemical and/or irradiation and/or a range of temperature;

(b) exposing the mixture of step (a) to said chemical and/or irradiation and/or said range of temperature for a time sufficient to regenerate the hydroxyl 3' end; and (c) conducting the amplification reaction.

The present invention also provides a method for amplification of a target ribonucleic acid sequence, the method comprising the steps of:

(a) contacting a sample suspected of containing the target ribonucleic acid with an amplification reaction mixture containing at least one first reversibly modified oligonucleotide, wherein the first reversibly modified oligonucleotide has a non-hydroxyl group 3' end which can be converted into a hydroxyl 3' end upon exposure to a first chemical and/or irradiation and/or a first range of temperature;

(b) incubating the mixture of step (a) under conditions that allows reverse transcription of the ribonucleic acid;

(c) exposing the mixture of step (b) to said first chemical and/or irradiation and/or said first range of temperature for a time sufficient to regenerate the hydroxyl 3' end of the first reversibly modified oligonucleotide; and (d) conducting the amplification reaction to form primer extension products.

In one embodiment of the method for amplification of a target ribonucleic acid sequence, the amplification reaction mixture further comprises at least one second reversibly modified oligonucleotide, wherein the second reversibly modified oligonucleotide has a non-hydroxyl group 3' end which can be converted into a hydroxyl 3' end upon exposure to a second chemical and/or irradiation and/or a second range of temperature; and wherein the method further comprises a step of exposing the mixture of step (a) to said second chemical and/or irradiation and/or said second range of temperature for a time sufficient to regenerate the hydroxyl 3' end of the second reversibly modified oligonucleotide before the step (b).

The present invention also provides a reversibly modified oligonucleotide having a non-hydroxyl group 3' end which can be converted into a hydroxyl 3' end upon exposure to a chemical and/or irradiation and/or a range of temperature.

The present invention also provides a nucleic acid amplification reaction mixture or kit comprising the reversibly modified oligonucleotide of the present invention.

Examples of the non-hydroxyl 3' end of the reversibly modified oligonucleotide of the present invention are, but not limited to, a carboxylic acid ester, a ether group including silyl ether, and a photolytic group.

In one preferred embodiment, the method of the invention is useful in a one-step RT-PCR process with a two-enzyme system, in which at lease a reverse transcriptase and a thermostable DNA polymerase is used, or with a one-enzyme system, in which only one enzyme is used which functions as both a reverse transcriptase and a DNA polymerase.

In another preferred embodiment, at least 25%, preferably at least 50%, more preferably at least 75%, and most preferably at least 90% of the non-hydroxyl group 3' end of the reversibly modified oligonucleotide of the invention is converted into a hydroxyl 3' end.

The oligonucleotide based controlled start nucleic acid amplification of the present invention, besides being an alternative hot-start technology, can improve the performance of various nucleic acid amplification reactions, especially the RT-PCR reactions.

In the presence of catalyst DMAP in TEA, hydroxyl groups of oligonucleotide, including both 5' and 3' hydroxyl group, form ester with maleic anhydride.

Figure 2:
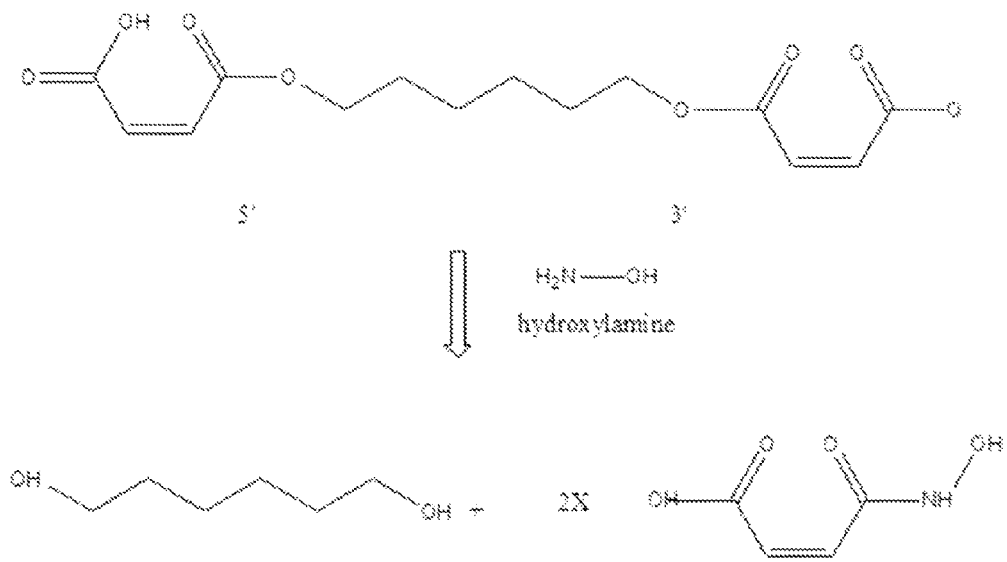

FIG. 2. Hydrolysis of maleic ester of oligonucleotide.

Hydroxylamine is a strong nucleophilic chemical and can effectively break carboxylic ester bond. As a result both 5' and 3' hydroxyl groups are regenerated and a hydroxyamide is formed.

Figure 3:
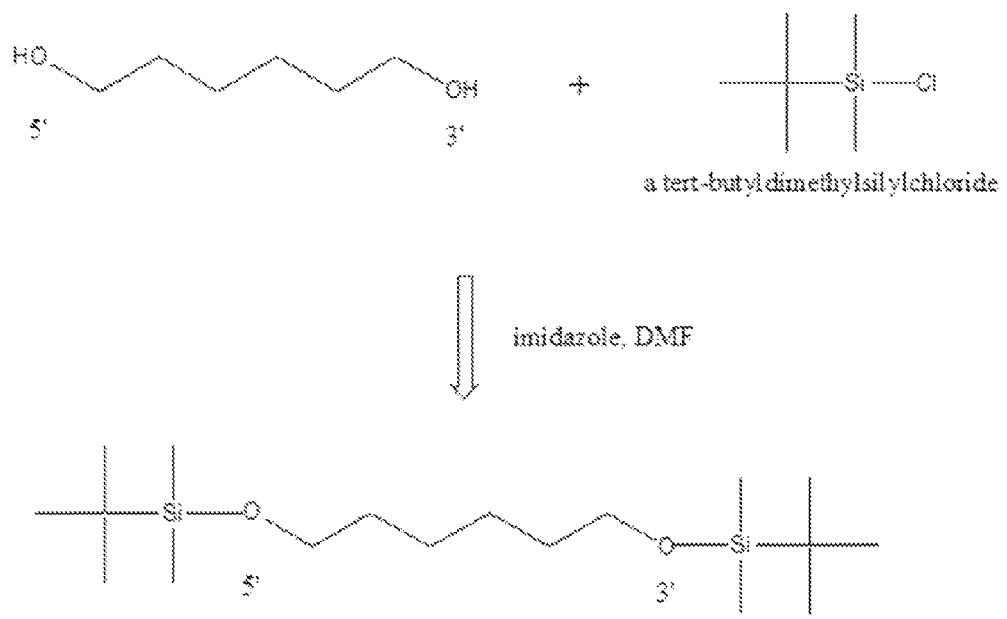

FIG. 3. Modification of oligonucleotide with a trialkylsilyl chloride.

5' and 3' hydroxyl groups of an oligonucleotide react with tert-butyldimethylsilyl chloride in the presence of imidazole to form tert-butyldimethylsilyl ether.

Figure 4:
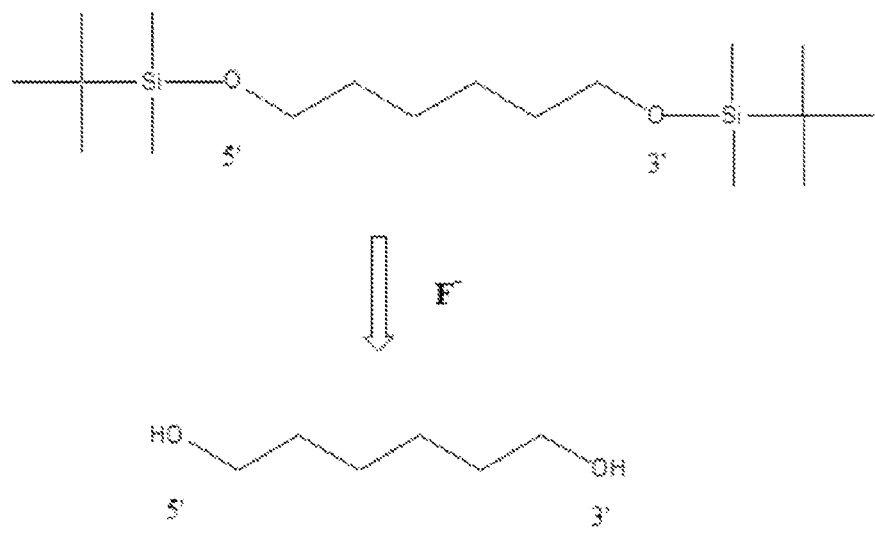

FIG. 4. Cleavage of silyl ether by fluoride.

Silyl ether is hydrolyzed by fluoride. Both 5' and 3' hydroxyl groups are regenerated as the result of the hydrolysis.

FIG. 5. Reduction of primer dimer formation with modified oligonucleotidein DNA PCR.

Figure 5A:
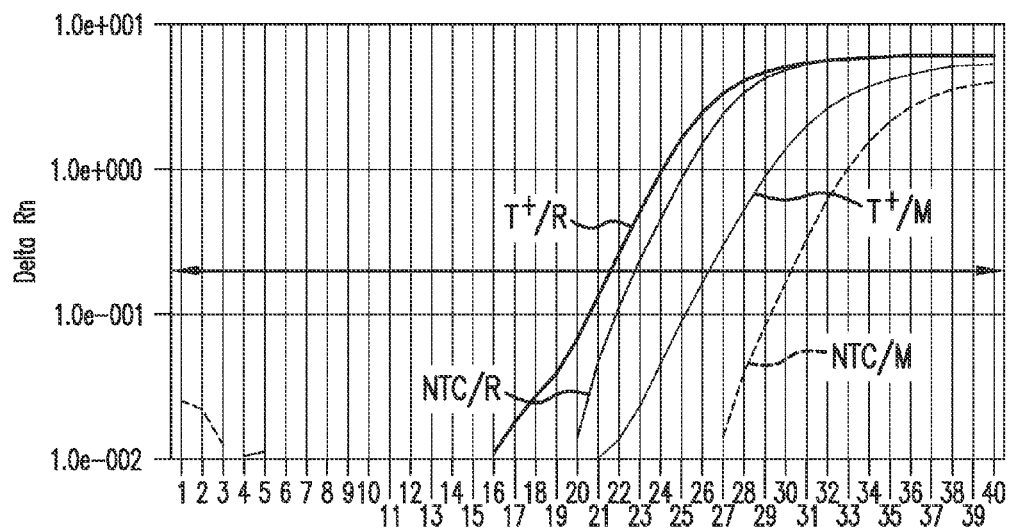
Figure 5B:
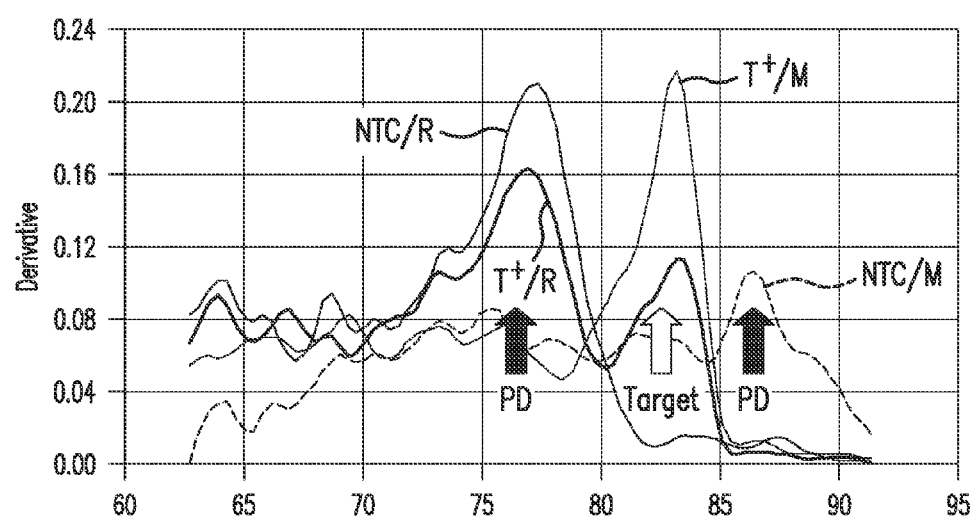

FIG. 5A is amplification curve with regular unmodified oligonucleotides (R) and modified oligonucleotide (M) in the presence of template ($T^+$) or absence of template, i.e., no template control (NTC). PCR was done with regular cold-start Taq polymerase. Amplification was monitored with Sybr Green™ dye, a double strand specific nucleic acid staining fluorophore. Sybr Green™ detects double stranded DNA in a non-sequence specific way. Therefore both amplified primer dimer and target sequence are detected. Primer dimer and target sequence are distinguished by melting curves of amplified products (FIG. 5B).

FIG. 6. Ineffectiveness of hot-start Taq DNA polymerase in preventing primer dimer formation under one-step RT PCR reaction condition with regular unmodified oligonucleotides.

Figure 6A:
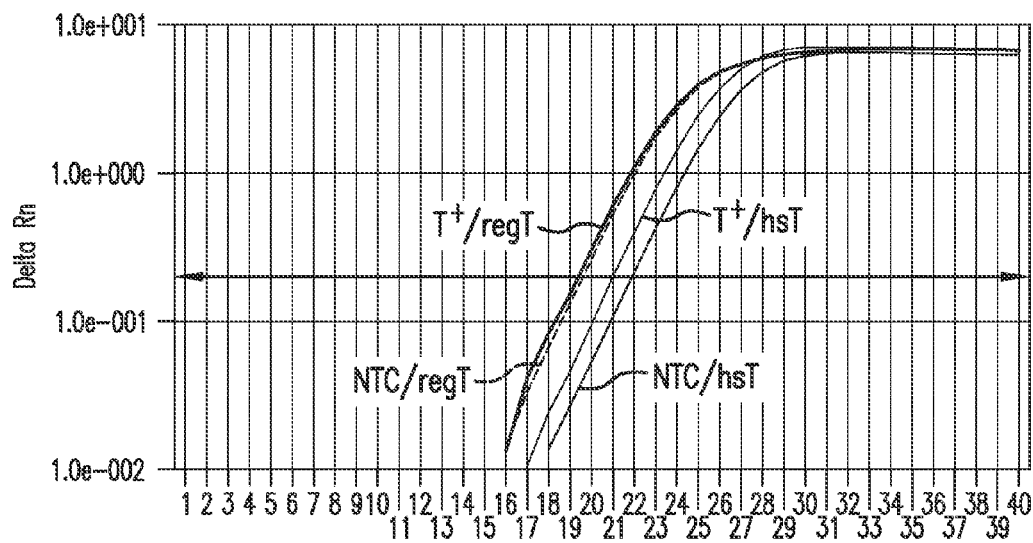
Figure 6B:
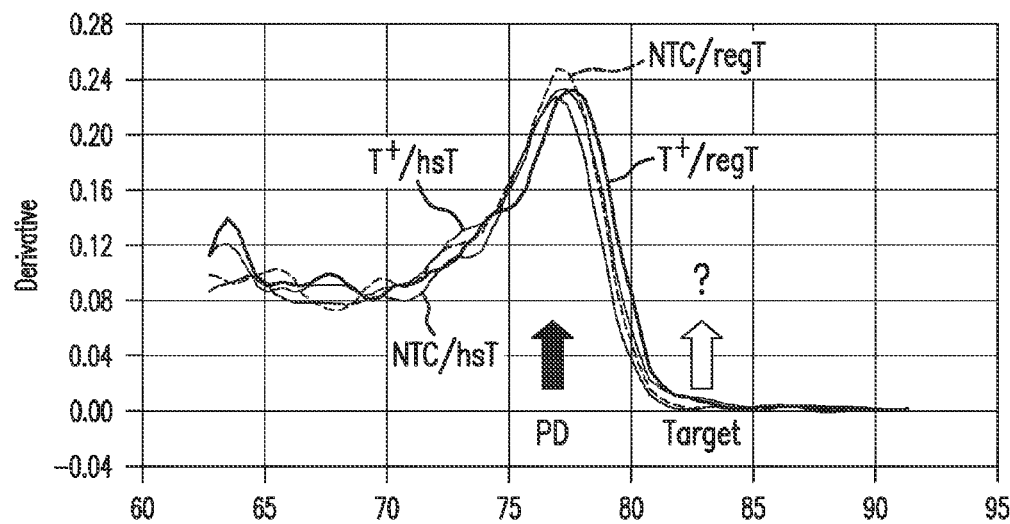

Under one-step RT PCR condition, both regular Taq DNA polymerase (regT) and hot-start Taq DNA polymerase (hsT) produced primer dimer only regardless presence of template ($T^+$) or absence of template (no template control, NTC). Amplification and melting curves are shown in FIG. 6A and 6B respectively.

Figure 7:
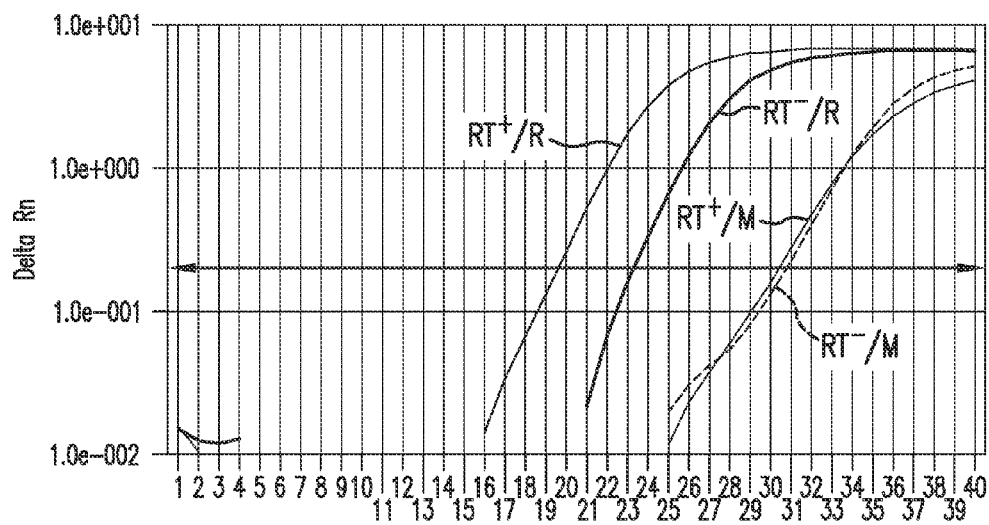

FIG. 7. Reduction of primer dimer formation by modified oligonucleotides.

All PCR reactions were done with regular Taq DNA polymerase in the absence of template. Therefore all products observed here are primer dimers. It is a way to measure how much primer dimer is formed under different conditions. The more primer dimer is formed, the earlier amplification curve arises.

Regular unmodified oligonucleotides (R) produced primer dimmer. Presence of reverse transcriptase ($RT^+$) led to more primer dimer formation than absence of reverse transcriptase ($RT^-$) as reflected in ~4 cycle difference in Ct value. In contrast, primer dimer is much reduced with modified oligonucleotides (M). Presence of reverse transcriptase did not lead to more primer dimer formation.

FIG. 8. Improvement of one-step RT PCR performance with modified oligonucleotides.

With modified oligonucleotides (M), Ct of primer dimer is delayed by 11 cycles in comparison to that of regular oligonucleotides (R). With regular oligonucleotides, severe primer dimer formation caused no amplification of target sequence even in the presence of 1,250 copies of target sequence (FIG. 8B). In contrast modified oligonucleotides gave clean amplification of target sequence without primer dimer as revealed by melting curve of amplified products.

FIG. 9. Number of possible species of primer dimers vs number of oligonucleotides present in an amplification system.

FIG. 9 is generated based on following assumptions:
1. Each target is amplified with two different oligonucleotides;
2. Each primer dimer (PD) is formed with two different oligonucleotides.
3. Any two oligonucleotides could form only one primer dimer.

Number of possible primer dimer species (#PD) is calculated with following equation:

$$\#PDs = N(2N-1)$$

N is number of targets to be amplified.

When N increases, number of oligonucleotides required increases linearly. Meanwhile #PD goes up geometrically. For example, there are two oligonucleotides in a single-plex amplification system. In such a single-plex system, there is only one target directed amplification and one species of primer dimer. Ratio of #PD/N is 1. In a deca-plex amplification system, there are twenty oligonucleotides and 10 target sequences. Now #PD is increased to 190. The ratio of #PD/N species becomes 19.

The geometrical increase in number of primer dimer species makes multiplex PCR very challenging especially in one-step RT PCR system in which chance of primer dimer formation is greatly increased.

DETAILED DESCRIPTION OF THE INVENTION

The present invention relates to a method for amplification of a target nucleic acid sequence or signal, wherein an amplification reaction mixture is used which contains at least one reversibly modified oligonucleotide having a non-hydroxyl group 3' end which can be converted into a hydroxyl 3' end upon exposure to a chemical and/or irradiation and/or a range of temperature.

As used herein, the term "nucleic acid amplification" refers to the amplification of the nucleic acid sequence (i.e. RCR, RT-PCR) or the amplification of the nucleic acid signal (i.e. invader assay).

Normally an oligonucleotide used in nucleic acid amplification has a 3' hydroxyl group. The 3'hydroxyl group is essential for the oligonucleotide: i. to be extended by a nucleic acid polymerase; and ii. to be ligated by a nucleic acid ligase. It also impacts: i. susceptibility to 3'→5'nuclease activity which is called proof-reading activity; and ii. formation of a cleavable structure in invader assay. Thus, modification of the 3'hydroxyl group of the oligonucleotide primer would effectively inhibit its function in the amplification reaction.

Criteria for choosing a proper modifying group are:
1. A process produces oligonucleotide with complete or near complete modification.
2. Modified oligonucleotide is stable under storage condition. Oligonucleotide is usually stored in aqueous solution at 4° C. or −20° C. Measurable automatic reversion under the condition does not occur.
3. Chemical used to reverse the modification and products arisen from cleavage do not interfere nucleic acid amplification process. Because it is preferred to do the controlled start in a homogeneous system without additional step of manipulation, it is important that the chemical and/or the cleaved products will neither inhibit enzyme (polymerase, ligase, nuclease etc.) activity significantly nor change specificity of the reaction.
4. Temperature at which reversion is effectively conducted is compatible with thermostability of enzyme for the reaction system. For example it would be the best to have reversion occurred at a temperature greater than 60° C. in a PCR system. For nucleic acid amplification by TMA, reversion should be done below 45° C.

In one preferred embodiment, the reversibly modified oligonucleotide of the invention has a 3' carboxylic acid ester. To regenerate 3' hydroxyl group, a chemical selected from but not limited to azide, imidazole, pyridine, hydroxylamine, hydrazine, tetrabutylammonium hydroxide, is used.

In another preferred embodiment, the reversibly modified oligonucleotide of the invention has a 3' silyl ether. To remove the 3' silyl group and regenerate 3' hydroxyl group, a chemical containing fluoride is included in the reaction system.

In another preferred embodiment, the reversibly modified oligonucleotide of the invention has a 3' ether group.

In another preferred embodiment, the reversibly modified oligonucleotide of the invention has a 3' modified group that can undergo photolytic cleavage to generate 3'hydroxyl group. The photolytic group is removed by light or in combination with a chemical.

Modifier of oligonucleotide of the present invention is attached to the oligonucleotide by:
1. Post synthesis modification.
2. Oligonucleotide synthesizer using a synthesis support having a modifier
3. Oligonucleotide synthesizer using a synthesis support having a modified nucleoside
4. Oligonucleotide synthesizer using a modified nucleoside phosphoramidite. Synthesis direction is either 5' to 3' or 3' to 5'.
5. Oligonucleotide synthesizer using a reagent In addition to improvement of qualitative amplification of nucleic acid by hot-start of PCR reaction, the invention disclosed here is capable to improve nucleic acid amplification by isothermal amplification qualitatively and quantitatively.

There are reports of quantitative detection of nucleic acid by various isothermal amplification technologies including SDA, TMA, NASBA, RCA (Walker, 1996; Spears, 1997; Nadeau, 1999; Leone, 1998; Nilsson, 2002, all of which are incorporated herein by reference). However, accuracy and precision of those assays clearly need to be improved. One cause of poor quantification is lack of controlled start of amplification reaction.

According to the present invention, an oligonucleotide used in nucleic acid amplification has a 3' moiety other than hydroxyl group. However 3' hydroxyl group can be generated by exposure to a chemical and/or irradiation and/or a range of temperature. Regeneration of 3' hydroxyl group enables nucleic acid amplification by:
1. Target sequence amplification by nucleic acid polymerase.

Polymerase mediated target sequence amplification processes include polymerase chain reaction (PCR), rolling circle amplification (RCA), strand displacement amplification (SDA), single primer isothermal amplification (SPIA™), exponential single primer isothermal amplification (X-SPIA™), loop mediated amplification (LAMP), nucleic acid sequence based amplification (NASBA), transcription mediated amplification (TMA), and self-sustained sequence replication (3SR).

3' hydroxyl group is required for nucleic acid polymerization reaction.

ii. Ligation mediated target sequence amplification.

In this category, ligation is a key step to get target sequence amplified. Technologies include ligase chain reaction (LCR), enabled LCR as described in U.S. Pat. No. 6,511,810; gap-LCR (U.S. Pat. No. 5,427,930), and ligation mediated PCR.

In ligation mediated PCR, ligation occurs before PCR process. Ligation is to add a primer sequence to target. Oligonucleotides for both ligation reaction and PCR are subject of the present invention.

iii. Invader assay

Invader assay (U.S. Pat. Nos. 6,348,314; 6,090,543; 6,001,567; 5,985,557; 5,846,717; and 5,837,450, all of which are incorporated herein by reference) is a signal amplification assay. Target template, an upstream invasive oligonucleotide and a down stream oligonucleotide that partially overlaps with the invasive oligonucleotide form an invasive structure. Flap endonuclease cleaves the downstream oligonucleotide to generate detection signal. It was found that 3' end of the invasive oligonucleotide affects cleavage greatly. As matter of fact, cleavage structure formed with invasive oligonucleotide having a non-hydroxyl 3' end showed dramatically reduced cleavage.

By suppressing primer dimer formation/non-specific reaction below reaction temperature and controlling reaction onset, the present invention will improve sensitivity and quantification capability of the above nucleic acid amplification methods.

The oligonucleotide of the present invention contains a sequence that is capable of specific hybridization to a desired target nucleic acid sequence. In one embodiment, the oligonucleotide contains a sequence complementary to a target nucleic acid sequence only. In another embodiment, it has a region not complementary to target sequence. The non-complementary sequence is located in 5' region of the oligonucleotide.

In another embodiment, the oligonucleotide of the present invention has a secondary structure that changes, e.g., diminishes or disappears upon duplex formation that is resulted from amplification.

Oligonucleotide may consist of five parts:
  i. Bases;
  ii. Sugar group
  iii. Linkage between nucleoside
  iv. A signal generation group for detection
  v. Other groups.

i. Bases include any natural bases, without any limitation, adenine, $N^6$-methyl adenine, $N^6$-isopentenyl adenine, guanine, 7-methyl guanine, queuosine, wyosine, inosine, cytosine, 3-methyl cytosine, 5-methyl cytosine, uracil, dihydrouracil, pseudouracil, 4-thiouracil, and thymine. Base analogs, which may also be used, include, without any limitation, 7-deaza-adenine, 7-deaza-guanine, 2-amino purine, 2,6-di-amino purine (adenine and guanine), 2- and/or 6-thio purine (adenine and guanine), 5-bromo uracil, 5-nitro indole, 5-propynyl uracil, iso-cytosine, iso-guanine 5-phenyl-uracil, 2-N-methylguanine, 5-butynyl-uracil, dimethylthiazole uracil, 5-propynyl cytocine, 5-phenyl-cytosine, 5-butynyl-cytosine, dimethylthiazole cytosine, 9-(aminoethoxy)phenoxazine, 5-(N-aminohexyl)carbamoyl-uracil, 6-azathymine, $N^2$-imidazolylpropyl-2-amino adenine, $N^2$-imidazolylpropyl-guanine, modified bases as disclosed in U.S. Pat. No. 6,001,611. The most commonly used bases are adenine, guanine, cytosine and thymine.

ii. Backbone of the oligonucleotide may consist of either a regular 5' to 3' phosphodiester bond or various modifications thereof. Examples of modifications include peptide linkage as seen in peptide nucleic acid (PNA), phosphorothioate, phosphorodithioate, N3'→O5' phosphoramidate, O3'-N5' phosphoramidate, 3' phosphorothiolate, 5' phosphorothiolate, inverted linkage, methylphosphonate, morpholino nucleic acid, boranophosphonate, phosphoro-N-butylamidates, and methylenemethylimines, d-spacer, and carbon linkers.

iii. The sugar group of the oligonucleotide used in the present invention usually is ribose and/or 2-deoxyribose. It may contain one or more other types of sugar moieties, e.g., 2-O-alkyl ribose, 2-amino ribose, 2-fluoro ribose, arabinose, 2-deoxy arabinose, 2-deoxy-2-fluoro arabinose, 1,5-anhydro hexitol, 2-O,4-C-methylene ribose as in locked nucleic acid (LNA), and cyclohexene backbone.

iv. According to the present invention, the oligonucleotide may include a signaling moiety. The moiety can be any that is suitable for detection by physical, chemical, photochemical, immunochemical, and biochemical methods including, but not limited to fluorescence, chemiluminescence, bioluminescence, electrochemiluminescence, phosphorescence, time-resolved spectrometry, fluorescence polarization, enzymatic reaction, radioactivity, colorimetry, mass spectrometry, magnetism, electrophoretic mobility, and chromatography.

In one embodiment, the signaling moiety includes an indicating moiety and a regulating moiety separated by a sequence that may form a cleavage site for a nuclease or a ribozyme. An example is Takara/Clontech's Q-zyme assay.

In another embodiment, the signaling moiety includes a labeled moiety and a quencher moiety that quenches the labeled moiety when the oligonucleotide is in single stranded state. Upon forming double-stranded structure, signal is generated. Amplifluor™ and Scorpion™ are two representative technologies of this category. Such interaction between the labeled moiety and the quencher moiety can be between any suitable entities including without any limitation small molecules, e.g., fluorophores and their quenchers and large molecules, e.g., protein molecules (Boute, 2002). The interaction can also be based on any suitable mechanism. For example, the labeled moiety and the quencher moiety can interact with each other based on resonance energy transfer including without any limitation fluorescence resonance energy transfer (FRET), luminanscence resonance energy transfer (LRET), phosphorescence resonance energy transfer (PRET), and bioluminescence resonance energy transfer (BRET).

Among various labeled moieties and quencher moieties, FRET probes have been widely used in detection of amplified target molecules. The most common FRET probe has two interactive moieties. One is fluorescence donor group and the other one is fluorescent acceptor group. Although the acceptor group can be fluorescent, it is preferred to have a non-fluorescent group as the acceptor. The donor group can be placed either at the 5' end, in the middle, or at the 3' end. So can the acceptor group. It is preferred to put the donor group at 5' end. Cleavage of probe by a structure specific nuclease when the probe hybridizes to a target nucleic acid will separate the donor group from the acceptor group and release quenching of the donor's fluorescence by the acceptor.

The signaling moiety of the probe of the present invention can also have more than two interactive moieties. For example, U.S. Pat. No. 5,952,180 discloses a method to make an extendable oligonucleotide with a distinguishable fluorescence emission spectrum. The unique fluorescence emission spectrum is generated by combinatorial fluorescence energy transfer tag. Another example relates to a wavelength-shifting probe with three interactive groups as disclosed in U.S. Pat. No. 6,037,130.

In yet another embodiment, oligonucleotide itself can be a regulating moiety that interacts with an indicating moiety. For example, Nurmi has reported synthesis of a singly labeled fluorescent terbium chelate probe and its use in detection of PCR products (Nurmi, 2000).

The oligonucleotide may also be part of binary or trinary signal generator. For example, the probe of the present invention can be a binary oligonucleotide prepared according to the methods disclosed in U.S. Pat. No. 6,432,642. Another binary probe containing two complementary oligonucleotides is described in Li et al. (Li, 2002). The probe of the present invention can also be a tripartite molecule prepared by the methods described for making a tripartite molecular beacon. (Nutiu, 2002). One difference would be that the oligonucleotide participates both amplification and detection reaction.

v. The oligonucleotide of the present invention may also contain groups at selected positions. The groups include, but not limited to, minor groove binder, pyrene, cholesterol, acridine, biotin, capillary electrophoresis mobility modifier, amine, carboxyl, phosphate, thiol to facilitate target binding, conjugation to surface or other molecules or detection by capillary electrophoresis.

Modification of hydroxyl groups on an oligonucleotide is a common practice to protect hydroxyl group, to label oligonucleotide, to add special functional group, to alter various properties such as nuclease resistance, binding affinity etc. For example, acetic anhydride in the presence of N-methylimidazole and tetrahydrofuran (THF) is used to do capping in automated oligonucleotide synthesis.

For the present invention, suitable modified group has to fulfill the following criteria:
1. Ability to regenerate 3' hydroxyl group.
It is preferred that 10% to 100% of modified oligonucleotide regenerates its 3' hydroxyl group. It is more preferred that at least 50% of modified oligonucleotide regenerates its 3' hydroxyl group. It is even more preferred that at least 75% of modified oligonucleotide regenerates its 3' hydroxyl group. It is the most preferred that at least 90% of modified oligonucleotide regenerates its 3' hydroxyl group. Regeneration can occur before nucleic acid amplification starts or happens gradually as amplification process proceeds.
2. A robust modification process produces oligonucleotide with complete or near complete modification. Presence of unmodified oligonucleotide in a nucleic acid amplification system could undermine benefit of this invention. Percentage of the unmodified oligonucleotide producing such a negative impact depends on a particular amplification system.
3. Modified oligonucleotide should be stable under storage condition with no measurable automatic reversion. Storage solution has to be compatible with nucleic acid amplification reaction system.
It should also have adequate stability in a reaction mix in which all reaction components are present. This is especially important for chemical assisted activation. It is preferred that elevated temperature can greatly accelerate activation process.
4. Condition of reverse reaction is compatible with nucleic acid amplification process. Activation of 3' modified oligonucleotide is preferentially done in the same reaction system as nucleic acid amplification system. Therefore chemical used for activation, products of activation, temperature, pH, ionic strength, solvent, wavelength and intensity of light in a photo-activation process etc. should be all compatible with nucleic acid amplification process.

An oligonucleotide of the present invention has a 3' group consisting of a non-hydroxyl group. Preferred groups are:
1. A carboxylic acid ester group
2. A ethers including silyl ether group
3. A photolytic group Modifier of oligonucleotide of the present invention is attached to the oligonucleotide by:
1. Post synthesis modification.
2. Oligonucleotide' synthesizer using a synthesis support having a modifier
3. Oligonucleotide synthesizer using a synthesis support having a modified nucleoside
4. Oligonucleotide synthesizer using a modified nucleoside phosphoramidite. Synthesis direction is either 5' to 3' or 3' to 5'.
5. Oligonucleotide synthesizer using a reagent Synthesis by an oligonucleotide synthesizer is more preferred than post synthesis modification.

When post synthesis modification is used to attach modifier group to 3' end, a free 5' hydroxyl group is very likely to be modified as well.

In one preferred embodiment, an oligonucleotide of the present invention has a 3' group consisting of a carboxylic acid ester group. Ester is selected from, but not limited to, formate ester, benzoylformate ester, haloacetate ester, methoxyacetate ester, triphenylmethoxyacetate ester, phenoxyacetate ester, maleate ester and its derivatives, succinate ester and its derivatives, 4-oxopentaoate ester, and pivaloate ester, crotonate ester, 4-methoxycrotonate ester, and 3-phenylpropionate.

To regenerate 3' hydroxyl group, a chemical is used. The chemical is from, but not limited to, azide, imidazole, pyridine, hydroxylamine, hydrazine, tetrabutylammonium hydroxide.

When acylation of oligonucleotide is done post synthesis, acylation of 3' hydroxyl group with anhydride requires basic solvent such as triethylamine (TEA), other basic solvents are pyridine, aniline, diethylamine, trimethylamine and pyrrolidone A catalyst, such as dimethylaminopyridine (DMAP), fluoride, 1-methylimidazole, 4-pyrrolinopyridine, 2-hydroxypyridine, is preferred to be present in the reaction.

In one preferred embodiment, the oligonucleotide of the invention has a 3'maleic acid ester. Hydroxylamine is used to regenerate 3'hydroxyl group.

In another embodiment, the oligonucleotide of the invention has a 3' silyl ether group.

The silyl ether is from a group consisting of trimethylsilyl ether, triethylsilyl ether, triisopropylsilyl ether, dimethylisopropylsilyl ether, diethylisopropylsilyl ether, dimethylthexylsilyl ether, t-butyldimethylsilyl ether, t-butyldiphenylsilyl ether, tribenzylsilyl ether, tri-p-xylsilyl ether, triphenylsilyl ether, diphenylmethylsilyl ether, and t-butylmethoxyphenylsilyl ether.

An —OH group can be converted to silyl ether by treating it with a trialkylsilyl chloride in the presence of a tertiary amine base such as imidazole, pyridine and triethylamine.

Silyl ethers are unaffected by most oxidizing and reducing agents, and are stable to most nonaqueous acids and bases. t-Butyldimethylsilyl group is stable in aqueous solution within the pH range 2 to 12, which makes it one of the most widely used hydroxyl modifying groups Stability of silyl ether has been well studied. Trimethylsilyl is the most readily silylated. However it is also the most labile to hydrolysis. Replacement of one of the methyl groups of the trimethylsilyl group by t-butyl gives a t-butyldimethylsilyl group, which is about $10^4$ folds more stable than the TMS group Silyl ether groups are most commonly removed by treatment with fluoride ion. Fluoride is from selected chemical group consisting of tetrabutylammonium fluoride, sodium fluoride, potassium fluoride, lithium fluoride, hydrofluoric acid.

In another preferred embodiment, the oligonucleotide of the invention has 3' ether group. A preferred ether group is tetrahydrofuranyl ether.

An ether group is allyl ether. The allyl ether is hydrolyzed by a palladium or rhodium catalyst.

Another ether group is p-methoxyphenyl or p-methoxybenzyl or 3,4-dimethoxybenzyl ether or (4-methoxyphenoxy)methyl ether. The ether is cleaved by ceric ammonium nitrate.

Ethers sensitive to Lewis acid catalyst mediated hydrolysis may also be used. The ethers include methoxyethoxymethyl (MEM) ether, methoxymethyl (MOM), guaiacolmethyl (GUM) ether, tetrahydropyranyl ether, tetrahydrothiofuranyl ether, Lewis acid catalysts suitable for the purpose are selected from $ZnX_2$, $MgX_2$, $AgX$, $CuX_2$, $MnX_2$, $SnX_2$, $FeX$, $CoX$, $PdX_2$, $HgX_2$, $FeX_3$, $AlX_3$, $LiBF_4$, $TiCl_4$, etc. X is a halogen atom.

3' Siloxymethyl ether or 2-(trimethylsilyl)ethoxylmethyl ether can be removed by fluoride from selected chemical group consisting of tetrabutylammonium fluoride, sodium fluoride, potassium fluoride, lithium fluoride, hydrofluoric acid.

3' 2-(Trimethylsilyl)dethoxymethyl ether is hydrolyzed by LiBF4 and/or fluoride to regenerate hydroxyl group.

3' Methyl ether is hydrolyzed with one or more chemicals from a group consisting of $BBr_3$, $SiCl_4$, NaI, and $AlX_3$.

In another preferred embodiment, the oligonucleotide of the invention has a 3' modified group that can undergo photolytic cleavage to regenerate 3'hydroxyl group. The 3' modified group is selected from chemical group containing p-methoxybenzyl ether, nitrate esters, and o-nitrobenzyl carbonate.

In addition to photolytic cleavage, a chemical may also be added into reaction system to reduce requirement for intensity and/or time of irradiation. For example, while p-methoxybenzyl ether is cleaved by UV light (>280 nm), ceric ammonium nitrate can be added into the reaction system to accelerate the hydrolysis reaction.

Kinetics and thermodynamics of modifier removal process can be affected by the modifying group, property of the chemical for activation, concentration of the chemical, temperature, other components in a reaction system such as pH, ionic strength, etc. If irradiation is used to regenerate 3' hydroxyl group, its intensity and wavelength can also affect speed and completeness of the activation process.

Application of the Present Invention in Various Nucleic Acid Amplification Processes To better understand how the present invention could be used in various nucleic acid amplification processes, the present invention is illustrated with respect to some of currently available nucleic acid amplification methods and enzymes involved.

Application of the Present Invention in Invader Assay

Invader assay is a signal amplification method and is disclosed in U.S. Pat. Nos. 6,348,314; 6,090,543; 6,001,567; 5,985,557; 5,846,717; and 5,837,450, all of which are incorporated herein by reference.

In invader assay, upstream invasive oligonucleotide and downstream signal generating probe oligonucleotide hybridize with target molecule and form a cleavage structure. Cleavage of hybridized probe by flap endonuclease generates detectable signal. Like other thermostable enzyme, flap endonuclease is active in a broad range of temperature. It is capable to cleave many structures in addition to the desired cleavage structures. Oligonucleotids present in a reaction system could form variety intra-molecular and inter-molecular structures. Most of them are only stable at low temperature. Cleavage of those structures results in either high background or low detectable signal. To reduce or even eliminate these unwanted cleavages can improve quality of the detection assay.

Use of oligonucleotide with modified 3' end, as disclosed herein, is a good way to reduce non-template dependent cleavage. It was reported that 3' group of upstream invasive oligonucleotide affects cleavage greatly (Kaiser, 1999). All substitutions of 3' hydroxyl group including 3' deoxy, 3' phosphate, and 3'd-spacer resulted in dramatic inhibition. In some cases the substitutions yielded nearly complete inhibition. It clearly demonstrated the importance of 3' hydroxyl group in the cleavage event. The present invention provides a method to use an oligonucleotide with a reversibly modified 3' end to control onset of invader assay in order to improve its quantification capability.

Invader assay is also capable to detect RNA molecule without reverse transcrition. RNA molecule is sensitive to heat, particularly in the presence of divalent metal ion such as $Mg^{2+}$, which is essential for the nuclease action. When RNA target is detected, hot-start condition is preferred to be mild. The present invention offers numerous modifiers with diverse activation conditions. A mild condition of activation can be easily identified. An example of mild activation is irradition which is gentle enough not to hurt target RNA molecules. In this aspect, the present invention has clear advantage over chemical modification based enzyme hot-start technologies.

Application of the Present Invention in Polymerase Chain Reaction

It has been well documented that hot-start can improve PCR amplification dramatically. Many hot-start methods have been developed to improve PCR amplification. They can be categorized into following groups:

i. Creation of a physical barrier separating components required for side reaction at low temperature.

U.S. Pat. Nos. 5,411,876, 5,565,339, 5,413,924 and 5,643,764 disclose arts to create such a barrier which disappears as temperature elevated. However it is inconvenient. Mixing of all components in such a heterogeneous system is also very challenging.

ii. Magnesium precipitation (U.S. Pat. No. 6,403,341)

Magnesium is a key element for DNA polymerase activity. According to the invention, magnesium is precipitated at low temperature and cannot participate DNA polymerization reaction. At an appropriate temperature, solubility of magnesium is increased. Consequently magnesium is released from the precipitate and activates the DNA polymerase. This is a heterogeneous hot-start system and faces similar problem as discussed in "i". Dispensing precipitated magnesium is hard to do.

iii. Reversible non-covalent binding of an inhibitory molecule to DNA polymerase.

Such an inhibitory molecule can be either an antibody (U.S. Pat. No. 5,338,671) or an oligonucleotide (U.S. Pat. Nos. 5,693,502, 5,874,557, 5,763,173, 6,020,130, and 6,183,967). Stability of inhibitor/DNA polymerase complex is temperature dependent. When temperature reaches to certain point, inhibitor falls off from DNA polymerase, which then becomes active. As a non-covalent inhibitor, complete inhibition is hard to be achieved. They also interfere with amplification to a certain degree, especially with oligonucleotide inhibitor.

iv. Chemical modification of DNA polymerase (U.S. Pat. Nos. 5,677,152, 5,773,258; and 6,183,998)

Like non-covalent inhibitors, these are homogeneous hot-start system. Dicarboxylic acid anhydride and aldehyde are used in those modifications respectively. Modifiers are removed from DNA polymerase with prolonged incubation at high temperature. DNA polymerase activity is restored with the removal of modifiers. They are very stringent in term of completion of enzyme activity suppression. However, the activation process is very harsh to the enzyme. As matter of fact, activation process itself denatures significant portion of enzyme molecules as well.

The present invention is also a chemical modification system. Instead of using chemically modified PCR enzyme, 3' modified oligonucleotide is used.

When DNA target is to be amplified by PCR, chemically reversibly modified oligonucleotides provide hot-start with high stringency just like chemically modified enzyme. Without being activated, 3' modified oligonucleotides can't be extended by DNA polymerase at low temperature. Therefore no primer dimer or side reaction could occur at low temperature. Diverse ways of activation, ranging from chemical assisted activation to irradition mediated activation, make it possible to have a mild activation condition.

When RNA target is to be amplified. RNA template has to be converted to DNA first via a process of reverse transcription. If reverse transcription is done in a separate tube and an aliquot of product of reverse transcription is used for PCR amplification, PCR process is essentially the same as that with DNA template as stated in the above.

One-step RT PCR is a process in which both reverse transcription and PCR are carried out in the same tube sequentially. As discussed in "BACKGROUND" session, none of the existing hot-start PCR is effective for one-step RT PCR. With the present invention, one-step RT PCR can be significantly improved.

For a single-plex one-step RT PCR, there will be only one oligonucleotide carrying a normal 3'hydroxyl group if the present invention is applied. This one is for reverse transcription. It is known that primer dimer can't arise from one single primer.

For a triplex one-step RT PCR process, such as Roche's product for donor blood testing in which presence of HIV, HBV and HCV is monitored, there are six primers. HIV and HCV are RNA targets and HBV is DNA target. There are 15 kinds of primer dimers could be formed with conventional technologies (FIG. 9). According to the present invention, 4 of the oligonucleotides have a 3' modified group. Therefore there will be only one kind of primer dimer could be generated. The advantage of current technology is obvious and significant.

By employing the present invention, one-step RT PCR can be further improved by using dual modifications. One modification is for oligonucleotides required for reverse transcription and the other one is for oligonucleotides participating PCR amplification. The two modifications have two different activation conditions so start of reverse transcription and PCR processes can be controlled separately. This approach will be especially helpful for multiplex one-step RT PCR. RT primer(s) will be activated and made available for RT reaction when reverse transcription is about to begin. Meanwhile the rest primers will remain inactivated until PCR starts. This will eliminate primer dimer formation/non-specific reaction occurred prior onset of RT. The step activation can be made in various ways. For example, one modification is removed by irradiation and the other is by chemical assisted activation. Another example is that both modifications have differential susceptibility to either the same chemical/irradiation. Temperature is another key factor affecting generation of 3' hydroxyl group.

Application of the Present Invention in Ligase Chain Reaction (LCR)

Like PCR, LCR is an exponential target amplification method involving thermocycling. Low sensitivity detection associated with LCR is largely attributed to residual activity of a thermostable ligase at temperature below its reaction temperature. In LCR, non-template directed amplification is indistinguishable from template-directed amplification.

Because 3'hydroxyl group is essential for ligation reaction, hot-start LCR with 3' modified oligonucleotides using invention disclosed herein can reduce or even eliminate non-template directed ligation at low temperature.

U.S. Pat. No. 6,511,810 discloses a method of using a thermostable flap endonuclease to enable ligation reaction. When a FRET probe is included in the system, it can be used to do real-time quantification of target molecules. While the invention significantly improves LCR detection, non-template directed amplification is not eliminated. The method disclosed herein can further reduce background. The present invention is well suited to perform hot-start in that process.

Application of the Present Invention in Rolling Circle Amplification (RCA), Strand Displacement Amplification (SDA), Single Primer Isothermal Amplification (SPIA$^+$), Exponential Single Primer Isothermal Amplification (X-SPIA$^+$), Loop Mediated Amplification (LAMP)

These arts are disclosed in U.S. Pat. Nos. 5,854,033; 6,183, 960; 6,210,884; 6,344,329, 5,270,184; 5,916,779; 6,251,639, and 6,410,278 respectively. A common component for all the above isothermal amplification processes is use of a DNA polymerase with strong strand displacement activity. The most widely used DNA polymerase in these technologies is. Bst DNA polymerase large fragment.

Although Bst DNA polymerase large fragment is active at temperature up to 65° C., it is not thermostable. Therefore chemical modification of enzyme is not viable way to do hot-start. As matter of fact, a hot-start system is yet to be developed for these technologies. Diverse activation condition associated with the present invention makes it possible to find a condition compatible with each particular amplification technology.

Application of the present invention to these assays can eliminate all side reactions occurred before start of amplification. Conventional oligonucleotides are replaced with oligonucleotides of the present invention. Ideally 3' hydroxyl group is regenerated when amplification reaction is about to start.

Application of the present invention to those processes not only can improve amplification sensitivity but also target quantification. Improved target quantification is achieved via controlled onset of amplification.

Use of the Present Invention in Association with NASBA, TMA, and 3SR

They are used primarily to amplify RNA target at a constant temperature. Amplification comprises following steps:

i. Reverse transcription to make complementary DNA (cDNA).

An RNA/DNA heterduplex is formed as result of the reverse transcription. Oligonucleotide used in the reverse transcription has a target binding sequence in 3' region and an RNA polymerase promoter region in 5' region. Single stranded promoter sequence is not transcriptionally functional until it becomes double stranded.

ii. RNase H degradation of RNA strand in RNA/DNA heteroduplex.

RNase H activity is provided either by the reverse transcriptase or a separate RNase H.

iii. Synthesis of double stranded DNA.

A second oligonucleotide hybridizes to the single stranded cDNA and is extended by the reverse transcriptase to generate a DNA/DNA duplex. Now promoter region for the corresponding RNA polymerase is double stranded and functional.

iv. Synthesis of single stranded RNA by in vitro transcription.

With a functional promoter and an RNA polymerase, each DNA/DNA duplex generates hundreds of RNA molecules. It completes a cycle of amplification. As a result, each RNA template molecule is amplified hundreds of times.

v. Repeats of steps i to iv.

This will amplify target nucleic acid exponentially.

Sensitivity of these assays in general is not as good as PCR. Their quantification capability is not as good as PCR either Application of controlled-start in these assays can improve those two important aspects. Controlled-start will effectively reduce or even eliminate side-reaction. This will improve assay sensitivity.

Use of the present invention in those processes will also improve their target quantification capability. Without a controlled-start system, amplification reaction starts rapidly right after all components are mixed. Different amplification onset time among samples and standards, in combination with fast amplification kinetics, makes accurate and precise quantification extremely difficult. Controlled-start will make all amplification start at the same time. Quantification can be significantly improved.

The oligonucleotide of the present invention is used in nucleic acid amplification to replace its conventional oligonucleotide counterpart that has a 3' hydroxyl group. Oligonucleotide sequence remains the same.

People of skill in the art will understand that magnitude of benefit of the present invention depends on nucleic acid amplification technology, sequence of oligonucleotide, reaction system, incubation condition etc.

People of skilled in the art are capable to make adjustment when the oligonucleotide of the present invention replaces conventional oligonucleotide. Depending on specific modifier group and chemical used to regenerate 3' hydroxyl group, it may be necessary to adjust oligonucleotide concentration, buffer system and incubation condition to achieve optimal reaction condition.

The present invention can be used in combination with other technologies which can reduce primer dimer formation/non-specific reaction. Hot-start technologies, as discussed earlier, are examples of such technologies. Single stranded DNA binding protein may also be included in reaction system to further reduce primer dimer formation and increase detection specificity.

Oligonucleotide of the present invention is compatible with using special bases and sugar groups in the first three nucleotides to further reduce primer dimer formation and non-specific reaction. Those two arts are disclosed in U.S. Pat. Nos. 6,001,611 and 6,794,142 respectively, both of which are incorporated herein by reference.

The present invention also relates to kits used to carry out nucleic acid amplification. Although configuration of each kit may vary, at least one oligonucleotide of the present invention is required to perform the amplification.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Modification of Oligonucleotide with Maleic Anhydride

Figure 1:
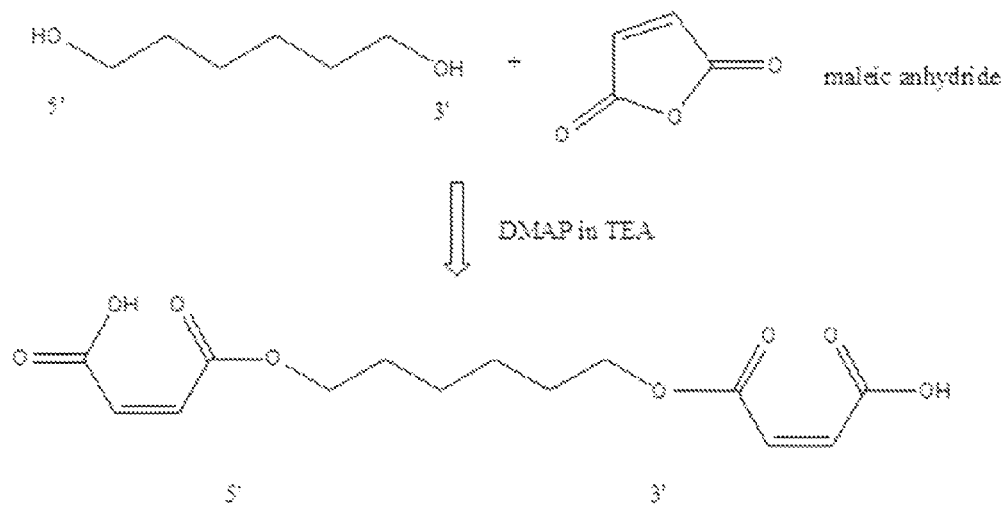
FIG. 1. Modification of oligonucleotide with an anhydride.

Mechanism of reaction is illustrated in FIG. 1. Sequences of three oligonucleotides used to detect Hepatitis B virus are listed in Table 1.

TABLE 1

| Sequence of oligonucleotide | |
|---|---|
| Oligonucleotide | Sequence |
| Forward primer: | CCG TCT GTG CCT TCT CAT CTG (SEQ ID NO: 1) |
| Reverse primer1 | GGT TTC CAT GTA ACG TGC AG (SEQ ID NO: 2) |
| Reverse primer2 | GGT CTC CAT GCG ACG TGC AG (SEQ ID NO: 3) |

Lyophilized oligonucleotides are dissolved in 1× TE (10 mM TrisHCl, pH8.0, 0.1 mM EDTA) at 100 µM. 4-(dimethylamino)-pyridine (DMAP)(Aldrich) solution is prepared in triethylamine (TEA)(Aldrich) at 3 mg/ml. 4M maleic anhydride (Aldrich) is prepared in N,N'-dimethyl formamide.(DMF)(Sigma).

Step 1. mix 16 µl of oligonucleotide with 320 µl of DMAP solution in a 2.0 ml microcentrifuge tube Step 2. add 6 µl of 4M maleic anhydride to the oligonucleotide/DMAP mixture Step 3. vortex at highest speed for 2 minutes at room temperature Step 4. add 1026 µl isopropanol and mix well Step 5. incubate at −20° C. for 2 hours Step 6. centrifuge at 14000 rpm for 20 minutes at 4° C.

Step 7. remove supernatant→add 800 µl of isopropanol→centrifuge at 14000 rpm for 20 minutes at 4° C.

Step 8. repeat step 7 once

Step 9. remove supernatant→dry the tube at room temperature→dissolve the oligonucleotide in water.

Example 2

Preparation of Taq DNA Polymerase

Thermus aquaticus (Taq) DNA polymerase gene was cloned via PCR with sequence from GeneBank (Accession No. J04639). Purification of Taq DNA polymerase was carried out with a procedure described by Lawyer et al. (Lawyer et al., 1989, JBC 264(11):6427-37; Lawyer et al. 1989, PCR Meth. Appl. 2(4):275-87).

Example 3

Modification of Taq DNA Polymerase with Citraconic Acid

Citraconic acid (Aldrich) and N,N'-dicyclohexyl carbodiimide (DCC) (Aldrich) and NHS (Aldrich) were all dissolved in DMF at 1M. 200 µl of DCC, 200 µl of NHS and 100 µl of citraconic acid were mixed in a 1.5 ml microcentrifuge tube. The mixture was then incubated at room temperature for 1 hour. The mixture was then centrifuged at 12,000 rpm for 20 minutes at room temperature. The pellet was discarded and the supernatant was kept to modify Taq DNA polymerase.

Purified Taq DNA polymerase is adjusted to 1 mg/ml in 20 mM MOPS, pH8.0 and 100 mM KCl. One volume of activated citraconic acid was mixed with 99 volume of Taq DNA polymerase. The mixture was then incubated at room temperature for 1 hour in order to result in inactivation of Taq DNA polymerase.

Example 4

PCR Amplification with Modified Oligonucleotides

Sybr Green preferentially binds to double stranded DNA with over 1000-fold higher affinity than single stranded DNA. It has been widely used to monitor PCR amplification at real-time. Although such binding is not sequence specific, it is possible to tell different amplified products by doing melting curve analysis because each amplified product has a certain melting temperature. Sybr Green assay was used in the invention to monitor primer dimer formation as well as amplification of target.

PCR system contains 50 mM TrisHCl, pH8.4, 5 mM KCl, 3 mM $MgCl_2$, 0.01% Tween-20, 0.005% gelatin, 1× Sybr Green, 500 nM 5-ROX, 7.5 mM hydroxylamine chloride (Aldrich), 0.2 mM each of dATP, dCTP, dGTP and TTP, 1 U of Taq DNA polymerase, 200 nM each of unmodified or maleid anhydride modified HBV primers. Reaction volume is 25 µl. 0 copy of HBV template (no template control or NTC) or 500 copies of HBV was added to the system.

Reactions were carried on ABI Prizm 7000. Thermocycling condition is as following: 95° C., 10 min→(95° C., 5 sec→60° C., 30 sec)×40 cycles.

To reverse the modification, both pre-incubation at high temperature, i.e., 95° C., 10 min, and presence of hydroxylamine chloride are important.

Results are shown in FIG. 5A. Compared with regular unmodified primers (NTC/R), NTC reaction with maleic anhydride modified primers (NTC/M) showed more than 7 cycles delayed amplification. In other words, NTC amplification or primer dimer formation was delayed by more than 7 cycles. It clearly demonstrated that modified primers are effective in reduction of primer dimer formation.

Example 5

Melting Curve Analysis of PCR Products

In FIG. 5A, HBV template plus reaction with regular primer ($T^+$/R) showed almost 5 cycles earlier amplification than HBV template plus reaction with modified primer ($T^+$/M). Without side reaction such as primer dimer formation, it is expected that both would have similar amplification kinetics because both contained the same number of HBV template. It requires further analysis of amplified products.

Melting curve analysis was conducted. Results are shown in FIG. 5B. HBV template plus reaction with regular primer ($T^+$/R) had two products, a major product which is primer dimer with melting temperature about 77° C., and a minor product which is template directed amplified product with melting temperature about 83° C. In contrast, HBV template plus reaction with modified primer ($T^+$/M) showed clean amplification. There is only template directed amplified product present.

Example 6

PCR with Regular Taq Polymerase and Chemically Modified Taq Polymerase in the Presence of Reverse Transcriptase Among various enzyme based hot-start PCR technologies, reversible chemical modification of PCR DNA polymerase is the most stringent and effective. It has been shown that it effectively improves DNA template amplification and allows multiplex PCR amplification.

However, in a one-step RT PCR system it faces difficulties which are stated in "BACKGROUND". A chemically modified enzyme was tested for its ability to reduce primer dimer formation in the presence of reverse transcriptase.

PCR system contains 50 mM TrisHCl, pH8.4, 5 mM KCl, 3 mM $MgCl_2$, 7.5 mM hydroxylamine chloride (Aldrich), 0.01% Tween-20, 0.005% gelatin, 500 nM 5-ROX, 1× Sybr Green, 0.2 mM each of dATP, dCTP, dGTP and TTP, 4 U of SuperScript III (Invitrogen), 200 nM each of unmodified HBV primers, 1 U of either regular non-hot-start or chemically modified hot-start Taq DNA polymerase. Reaction volume is 25 µl. 0 copy of HBV template (no template control or NTC) or 500 copies of HBV was added to the system.

Reactions were carried on ABI Prizm 7000. Thermocycling condition is as following: 55° C., 15 min→95° C., 10 min→(95° C., 5 sec→60° C., 30 sec)×40 cycles.

Amplification is shown in FIG. 6A. Although NTC amplification with chemically modified Taq (NTC/hsT) was delayed by about 2 cycles in comparison to regular Taq (NTC/regT), the NTC amplification with chemically modified Taq is very severe. In HBV template plus reactions, amplification with both regular Taq and chemically modified Taq reached threshold earlier than usual (see FIG. 5A for reference). Melting curve analysis revealed that there was only primer dimer in all four kinds of amplification in the experiment (FIG. 6B). This demonstrated that: i. reverse transcriptase can mediate primer dimer formation; ii. chemically modified PCR enzyme is ineffective in reducing primer dimer formation when reverse transcriptase is present in the reaction system.

Example 7

PCR with Modified Oligonucleotide

In order to further demonstrate both role of reverse transcriptase in promoting primer dimer formation and effectiveness of reversibly modified primers in preventing primer dimer formation, the following experiment was conducted:

PCR system contains 50 mM TrisHCl, pH8.4, 5 mM KCl, 3 mM $MgCl_2$, 7.5 mM hydroxylamine chloride (Aldrich), 0.01% Tween-20, 0.005% gelatin, 500 nM 5-ROX, 1× Sybr Green, 0.2 mM each of dATP, dCTP, dGTP and TTP, 1 U of regular unmodified Taq DNA polymerase, 0 U or 4 U of SuperScript III (Invitrogen), 200 nM each of unmodified or modified HBV primers. Reaction volume is 25 µl. No HBV template was added to the system.

Reactions were carried on ABI Prizm 7000. Thermocycling condition is as following: 55° C., 15 min→95° C., 10 min→(95° C., 5 sec→60° C., 30 sec)×40 cycles.

With regular unmodified primers, presence of reverse transcriptase in a NTC reaction (RT+/R) resulted in significantly more primer dimer (FIG. 7) than absence of reverse transcriptase (RT−/R), nearly 4 cycles earlier.

Modified primers reduced primer dimer formation dramatically. In the absence or presence of 4 U of reverse transcriptase, primer dimer formation was delayed by 7 (RT−/R vs RT−/M) and 11 cycles (RT+/R vs RT+/M) respectively when they are compared with regular primers. More importantly it showed that presence of reverse transcriptase did not significantly impact primer dimer formation when modified primers were used (RT−/M vs RT+/M).

Example 8

Target Amplification with Modified Primers

To further show effectiveness of reversibly modified primers in improving PCR amplification in one-step RT PCR setting, the following experiment was conducted:

PCR system contains 50 mM TrisHCl, pH8.4, 5 mM KCl, 3 mM $MgCl_2$, 7.5 mM hydroxylamine chloride (Aldrich), 0.01% Tween-20, 0.005% gelatin, 500 nM 5-ROX, 1× Sybr Green, 0.2 mM each of dATP, dCTP, dGTP and TTP, 1 U of regular unmodified Taq DNA polymerase, 4 U of SuperScript III (Invitrogen), 200 nM each of unmodified or modified HBV primers. Reaction volume is 25 µl. 0 copy of HBV template (no template control or NTC) or 500 copies of HBV was added to the system.

Reactions were carried on ABI Prizm 7000. Thermocycling condition is as following: 55° C., 15 min→95° C., 10 min→(95° C., 5 sec→60° C., 30 sec)×40 cycles.

Figure 8A:
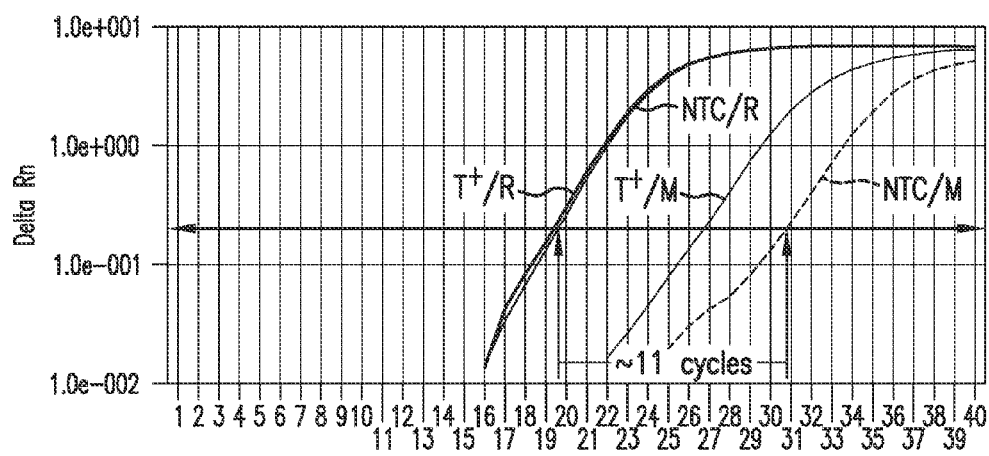
Figures 8B, 9:
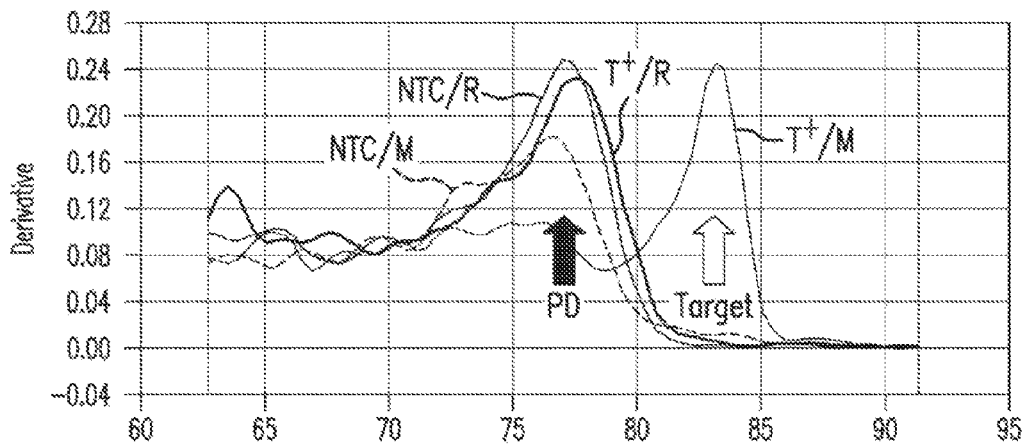

As shown in FIG. 8A, modified primers effectively reduced primer dimer formation by 11 cycles (NTC/M vs NTC/R). Template directed amplification with modified primers (T+/M) was free of primer dimer as demonstrated in FIG. 8B while amplification with regular primers only yielded primer dimer even in the presence of 500 copies of HBV template (T+/R in FIG. 8A and 8B).

REFERENCES

US Patent Documents

| 5,338,671 | August 1994 | Scalice et al. | 435/91.2 |
|---|---|---|---|
| 5,411,876 | May 1995 | Bloch et al. | 435/6 |
| 5,413,924 | May 1995 | Kosak et al. | 435/91.1 |
| 5,427,930 | June 1995 | Birkenmeyer et al. | 435/91.52 |
| 5,565,339 | October 1996 | Bloch et al. | 435/6 |
| 5,643,764 | July 1997 | Kosak et al. | 435/91.1 |
| 5,677,152 | October 1997 | Birch et al. | 435/91.2 |
| 5,773,258 | June 1998 | Birch et al. | 435/91.2 |
| 5,693,502 | December 1997 | Gold et al. | 435/91.2 |
| 5,763,173 | June 1998 | Gold et al. | 435/6 |
| 5,773,258 | June 1998 | Birch et al. | 435/91.2 |
| 5,874,557 | February 1999 | Gold et al. | 536/22.1 |
| 6,001,611 | December 1999 | Will | 435/91.2 |
| 6,020,130 | February 2000 | Gold et al. | 435/6 |
| 6,183,967 | February 2001 | Jayasena et al. | 435/6 |
| 6,183,998 | February 2001 | Ivanov et al. | 435/91.2 |
| 6,403,341 | June 2002 | Barnes et al. | 435/91.2 |
| 6,511,810 | January 2003 | Bi et al. | 435/6 |
| 6,794,142 | September 2004 | Laird et al. | 435/6 |

OTHER PUBLICATIONS

Kaiser et al., 1999, "A comparison of eubacterial and archaeal structure-specific 5'-exonucleases" J. Biol. Chem. 274(30): 21387-21394.

Leone et al., 1998, "Molecular beacon probes combined with amplification by NABSA enable homogeneous, real-time detection of RNA" Nucleic Acids Res. 26(9): 2150-2155.

Nadeau et al., 1999, "Real-time, sequence-specific detection of nucleic acids during strand displacement amplification" Anal. Biochem. 276: 177-187.

Nilsson et al., 2002, "Real-time monitoring of rolling-circle amplification using a modified molecular beacon design" Nucleic Acids Res. 30(14): e66.

Spears et al., 1997, "Simultaneous strand displacement amplification and fluorescence polarization detection of Chlamydia trachomatis DNA" Anal. Biochem. 247: 130-137.

Walker et al., 1996, "DNA detection by strand displacement amplification and fluorescence polarization with signal enhancement using a DNA binding protein" Nucleic Acids Res. 24(2): 348-353.

I claim:

1. A method for regenerating a 3' hydroxyl group, the method comprising:
   using a mixture comprising at least one reversibly modified oligonucleotide having a non-hydroxyl group 3' end which can be converted into a 3' hydroxyl group, wherein the oligonucleotide has a carboxylic acid ester group at its 3' end;
   exposing the mixture to a first chemical and a first range of temperature, wherein the first chemical and the first range of temperature regenerate the 3' hydroxyl group; and
   regenerating the 3' hydroxyl group of the at least one reversibly modified oligonucleotide having a non-hydroxyl 3' end.

2. The method of claim 1, further comprising:
   contacting a sample suspected of containing a target nucleic acid with the mixture comprising the at least one reversibly modified oligonucleotide with a regenerated 3' hydroxyl group; and
   conducting an amplification reaction.

3. The method of claim 2, wherein the target nucleic acid is ribonucleic acid, and wherein reverse transcription of the ribonucleic acid is conducted prior to the amplification reaction.

4. The method of claim 3, wherein the mixture further comprises at least one second reversibly modified oligonucleotide, wherein the at least one second reversibly modified oligonucleotide has a non-hydroxyl group 3' end which can be converted into a hydroxyl 3' end; and wherein the method further comprises exposing the mixture to a second chemical and a second range of temperature and regenerating the hydroxyl 3' end of the at least one second reversibly modified oligonucleotide having a non-hydroxyl 3' end.

5. The method of claim 3, wherein amplification of the ribonucleic acid is a one-step RT-PCR process with a two-enzyme system, in which at least a reverse transcriptase and a thermostable DNA polymerase is used, or is a one-step RT-PCR process with a one-enzyme system, in which only one enzyme is used which functions as both a reverse transcriptase and a DNA polymerase.

6. The method of claim 1, wherein the carboxylic acid ester is selected from the group consisting of formate ester, benzoylformate ester, haloacetate ester, methoxyacetate ester, triphenylmethoxyacetate ester, phenoxyacetate ester, maleate ester and its derivatives, succinate ester and its derivatives, 4-oxopentaoate ester, pivaloate ester, crotonate ester, 4-methoxycrotonate ester, and 3-phenylpropionate.

7. The method of claim 6, wherein the first chemical is selected from the group consisting of azide, imidazole, pyridine, hydroxylamine, hydrazine, and tetrabutylammonium hydroxide.

8. The method of claim 7, wherein the carboxylic acid ester is maleic acid ester, and the first chemical is hydroxylamine or hydrazine.

9. A method for regenerating a 3' hydroxyl group, the method comprising:
   using a mixture comprising at least one reversibly modified oligonucleotide having a non-hydroxyl group 3' end which can be converted into a 3' hydroxyl group, wherein the at least one reversibly modified oligonucleotide has a silyl ether group at its 3' end;
   exposing the mixture to a first chemical and a first range of temperature, wherein the first chemical and the first range of temperature regenerate the 3' hydroxyl group; and
   regenerating the 3' hydroxyl group of the at least one reversibly modified oligonucleotide having a non-hydroxyl 3' end.

10. The method of claim 9, wherein the first chemical is a fluoride selected from the group consisting of tetrabutylammonium fluoride, sodium fluoride, potassium fluoride, lithium fluoride, and hydrofluoric acid.

11. A method for regenerating a 3' hydroxyl group, the method comprising:
    using a mixture comprising at least one reversibly modified oligonucleotide having a non-hydroxyl group 3' end which can be converted into a 3' hydroxyl group, wherein the at least one reversibly modified oligonucleotide has an ether group at its 3' end;
    exposing the mixture to a first chemical and a first range of temperature, wherein the first chemical and the first range of temperature regenerate the 3' hydroxyl group; and
    regenerating the 3' hydroxyl group of the at least one reversibly modified oligonucleotide having a non-hydroxyl 3' end.

12. The method of claim 11, wherein the ether group is selected from the group consisting of tetrahydrofuranyl ether, allyl ether, p-methoxyphenyl ether, p-methoxybenzyl ether, 3,4-dimethoxybenzyl ether, (4-methoxyphenoxy)methyl ether, methoxyethoxymethyl ether, methoxymethyl ether, guaiacolmethyl ether, tetrahydropyranyl ether, tetrahydrothiofuranyl ether, siloxymethyl ether or 2-(trimethylsilyl)ethoxylmethyl ether, 2-(Trimethylsilyl)dethoxymethyl ether, and methyl ether.

13. The method of claim 12, wherein the ether is p-methoxyphenyl or p-methoxybenzyl or 3,4-dimethoxybenzyl ether or (4-methoxyphenoxy)methyl ether, and the first chemical is ceric ammonium nitrate.

14. The method of claim 12, wherein the first chemical is a Lewis acid catalyst, and the ether is selected from the group consisting of methoxyethoxymethyl ether, methoxymethyl ether, guaiacolmethyl ether, tetrahydropyranyl ether, and tetrahydrothiofuranyl ether.

15. The method of claim 12, wherein the first chemical is fluoride and the ether is siloxymethyl ether or 2-(trimethylsilyl)ethoxylmethyl ether.

16. The method of claim 12, wherein the first chemical is $LiBF_4$ and/or fluoride and the ether is 2-(Trimethylsilyl)dethoxymethyl ether.

17. The method of claim 12, wherein the ether is methyl ether, and the first chemical is selected from the group consisting of $BBr_3$, $SiCl_4$, NaI, and $AlX_3$.

18. The method of claim 2, wherein the amplification reaction is selected from the group consisting of invader assay, polymerase chain reaction, ligase chain reaction, rolling circle amplification, strand displacement amplification, transcription mediated amplification, nucleic acid sequence based amplification, self-sustained sequence replication, single primer isothermal amplification, exponential single primer isothermal amplification and loop mediated amplification.

19. The method of claim 9, wherein the silyl ether group is selected from the group consisting of trimethylsilyl ether, triethylsilyl ether, triisopropylsilyl ether, dimethylisopropylsilyl ether, diethylisopropylsilyl ether, dimethylthexylsilyl ether, t-butyldimethylsilyl ether, t-butyldiphenylsilyl ether, tribenzylsilyl ether, tri-p-xylsilyl ether, triphenylsilyl ether, diphenylmethylsilyl ether, and t-butylmethoxyphenylsilyl ether.

20. The method of claim 12, wherein the ether is allyl ether, and the first chemical is a palladium or rhodium catalyst.

21. The method of claim 9, further comprising:
contacting a sample suspected of containing a target nucleic acid with the mixture comprising the at least one reversibly modified oligonucleotide with a regenerated 3' hydroxyl group; and
conducting an amplification reaction.

22. The method of claim 11, further comprising:
contacting a sample suspected of containing a target nucleic acid with the mixture comprising the at least one reversibly modified oligonucleotide with a regenerated 3' hydroxyl group; and
conducting an amplification reaction.

23. A method for regenerating 3' hydroxyl groups, the method comprising:
using a mixture comprising at least two reversibly modified oligonucleotides, wherein each oligonucleotide has a different non-hydroxyl group 3' end which can be converted into 3' hydroxyl group, wherein the non-hydroxyl group is a carboxylic acid ester, a silyl ether, or an ether, and
exposing the mixture to two different chemicals and at least one range of temperature, wherein the chemicals and the range of temperature regenerate the 3' hydroxyl groups.

24. The method of claim 23, further comprising:
contacting a sample suspected of containing a target nucleic acid with the mixture comprising the at least two reversibly modified oligonucleotides, each with a regenerated 3' hydroxyl group, and
conducting an amplification reaction.

25. The method of claim 24, wherein the target nucleic acid is ribonucleic acid, and wherein reverse transcription of the ribonucleic acid is conducted prior to the amplification reaction.

* * * * *